United States Patent [19]

Gallagher

[11] 3,990,727
[45] Nov. 9, 1976

[54] QUICK DETACHABLE COUPLER
[76] Inventor: Stephen Franics Gallagher, 23 Eisenhower Drive, Norton, Mass. 02766
[22] Filed: Jan. 26, 1976
[21] Appl. No.: 652,176

[52] U.S. Cl. ............................ 285/26; 285/137 R; 285/423; 285/330; 285/DIG. 22; 339/61 C
[51] Int. Cl.² ......................................... F16L 35/00
[58] Field of Search ............ 285/DIG. 22, 423, 319, 285/320, 330, 260, 305, 26, 69, 137 R; 339/61, 91

[56] References Cited
UNITED STATES PATENTS

| | | | |
|---|---|---|---|
| 2,366,067 | 12/1944 | Smith | 285/260 X |
| 3,394,954 | 7/1968 | Sarns | 285/423 X |
| 3,588,149 | 6/1971 | Demler | 285/137 R |
| 3,603,621 | 9/1971 | Parsons | 285/319 |
| 3,686,896 | 8/1972 | Rutter | 285/320 |

FOREIGN PATENTS OR APPLICATIONS
1,164,335  9/1969  United Kingdom ............. 285/137 R OTHER PUBLICATIONS
Cromer, Electronics Inc., Catalog, 85 Wells Ave., Newton, Mass., p. 616.

Primary Examiner—Dave W. Arola
Attorney, Agent, or Firm—Russell & Nields

[57] ABSTRACT

A quick detachable coupler having a tubular female member receiving a tubular male member. The end of the female member into which the male member is inserted consists of a stiff continuous ring of resilient material provided with a pair of diametrically disposed latches and with a pair of diametrically disposed pressure portions. The male member is formed with an external latching and locking ring having a lead surface which engages corresponding lead surfaces on the latches to spread the latches against the spring pressure of the resilient ring to allow the male ring to travel past said latches and to be locked in position within said female member by locking surfaces on the latches engaging corresponding locking surfaces on the male locking ring. To release the male member from the female member, the pressure portions are squeezed together to produce a slight flattening of the female ring which spreads the latches apart sufficiently to release said male locking ring.

13 Claims, 7 Drawing Figures

QUICK DETACHABLE COUPLER

BACKGROUND OF THE INVENTION

This invention relates to the field of quick detachable couplers for devices such as pipes or conduits for conducting fluids. Despite the large number of such devices in the prior art, a need has existed, particularly in the surgical field, for a simple coupler whereby two conduits not only may be locked together by simply inserting one part of a two part coupler into the other, but also whereby the two parts may be readily separated from each other with a minimum of motion being imparted to the coupling member connected to an object sensitive to such motion, such as a surgical patient. Also the demands for such a device have required that it be simple and that each of its two parts be of a single piece construction, such as may be formed by injection molding of plastic material.

SUMMARY OF THE INVENTION

The present invention meets all of the above requirements by making the end of one of the coupling members in the form of a stiff continuous ring of resilient material provided with a pair of diametrically opposed latches and also provided with a pair of diametrically opposed pressure portions of increased wall thickness, the line between said pressure portions being substantially transverse to the line between said latches. The cooperating coupling member is provided with a rigid external locking ring which rides along inclined surfaces on the latches to deflect the latches outwardly until the ring passes below the latches whereupon the spring action of the end ring of the first member forces the latches into locking position over the locking ring and forces the end of the second member into firm contact with a cooperating portion of the first member. When it is desired to separate the two coupling members, pressure is applied usually be the fingers of the operator, inwardly on the two opposed pressure portions. This flexes the thinner wall portions of the end ring member to produce a hinging action which moves the opposed latches radially outward by a sufficient distance to clear the locking ring whereby the two coupling members may be freely separated.

DETAILED DESCRIPTION OF THE PREFERRED EMBODIMENT

Figure 1:
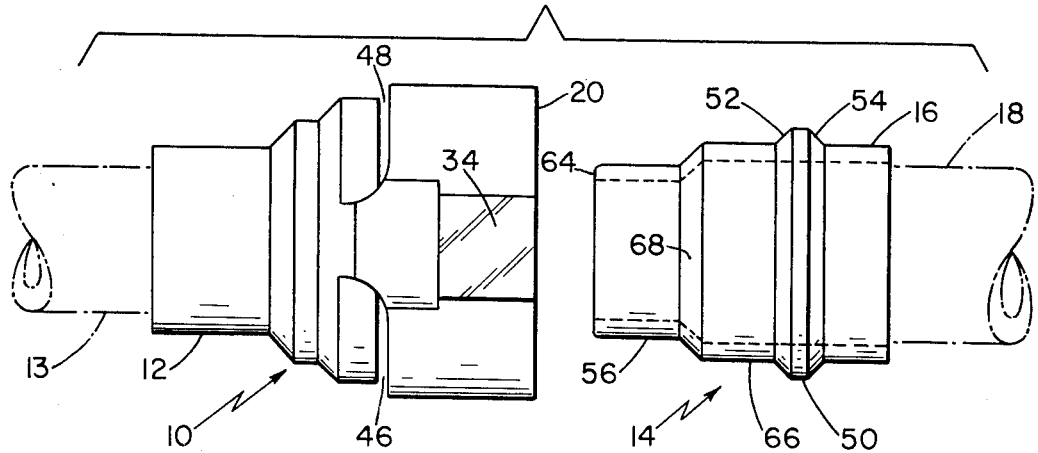
FIG. 1 is a side view of the two coupling members prior to being coupled to each other.

In the drawings, 10 is a female coupling member provided with an outer tubular member 12 which is adapted to receive a pipe or conduit 15 sealed to said member 12 in any suitable manner as, for example, by cementing. A male coupling member 15 is also provided with an outer tubular member 16 which likewise receives a pipe or conduit 18. The members 10 and 14 when connected together provided a fluid-tight connection between pipes 14 and 18. Members 10 and 14 are preferably each molded in one piece of a moldable plastic material such as the polymer resin Delrin.

Figure 2:
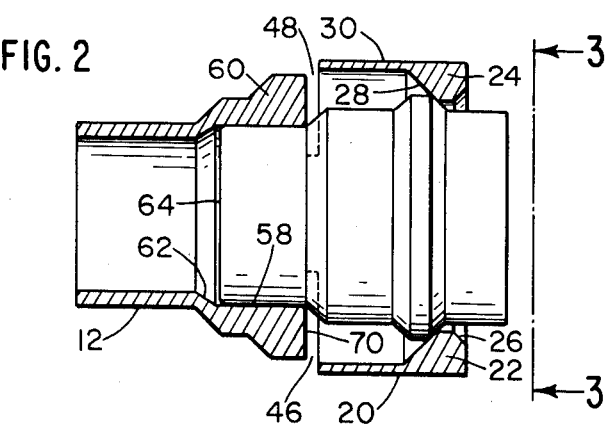
FIG. 2 is a view of the female coupling member in vertical cross-section with the male coupling member locked in the coupling position.

The end of member 10 opposite tubular member 12 is formed of a ring 20 formed with two diametrically disposed latches 22 and 24 projecting inwardly and extending for a limited distance, typically about 30° around the interior of ring 20. Each latch has a pyramidal cross-section, as shown in FIG. 2, with an inclined outer lead surface 26 and an inner inclined locking surface 28. The wall 30 of ring 20 is relatively thin so as to constitute ring 20 as a rather stiff spring capable of being slightly flattened by applying a compressive or expansive force diametrically across the ring. In order to provide means for applying such a compressive force, the wall of ring 20 is made with thicker sections 31 and 32, provided externally with flat finger pads 34 and 36. The finger pads 34, 36 are diametrically opposed in a direction transverse to the direction along which the latches 22 and 24 are opposed to each other. Since the thickness of the wall of ring 20 is increased at the latches 22 and 24 and at the finger pads 34 and 36, the flexibility of ring 20 is greatest at points 38, 40, 42, 44 intermediate the latches 22 and 24 and the finger pads 34 and 36. Therefore, when a compressive force is applied across the finger pads 34 and 36, in the direction of the arrows P-P in FIG. 4, by the fingers of the operator, maximum flexing of ring 20 will occur in the vicinity of points 38 — 44 and the latches 22 and 24 will move outwardly in the direction of the arrows X—X in FIG. 4 as the ring 20 is slightly flattened by such compressive force. Since maximum flexibility exists adjacent the points 38 — 44, the hinging action of the thin wall 30, during the motion of latches 22 and 24, is also a maximum adjacent these points. Member 10 may also be provided with a pair of strain-relief slots 46 and 48 at the inner end of ring 20. Such slots, while not essential to the basic operation of the device, nevertheless provide a freer latching action of the latches 22 and 24. The relative position of slots 46 and 48 to the latches 22 and 24 may be arranged so that they are 90 degrees apart form each other, leaving slots 46 and 48 in-line with finger pads 34 and 36 instead of in-line with latches 22 and 24 as shown in FIG. 1 and FIG. 2.

A latching and locking ring 50 is provided around the male coupling member 14 adjacent its outer end. Ring 50 formed with an inclined lead surface 52 adapted to cooperate with the lead surface 26 of the latches 22 and 24. Ring 50 is also provided with an outer inclined locking surface 54 adapted to cooperate with the locking surface 28 of the latches 22 and 24. In order to properly guide coupling member 14 into coupling position within coupling member 10 in which the desired forces are properly applied to the latches, member 14 is provided with a tubular extension 56 having an outer diameter to fit snugly within a bore 58 formed within a thickened wall section 60 of member 10. An inclined surface 62 connects the bore 58 to the smaller inner diameter of tubular member 12. When the member 14 is initially inserted into the open end of member 10, extension 56 enters the right-hand end of bore 58, thus insuring accurate alignment to the members 14 and 10 in the subsequent locking and sealing operation.

The extension 56 will have penetrated the bore 58 for only a limited distance when the lead surface 52 of locking ring 50 engages the lead surfaces 26 of the latches 22 and 24. As the insertion of member 14 continues, the lead surface 52 will force the lead surfaces 26 outwardly, thus exerting an expansive pressure in the direction of the arrows X—X in FIG. 4. In this way the motion of the latches 22 and 24 as described above in connection with FIG. 4 will be produced. When the lead surface 52 has passed over the lead surfaces 26, the locking surfaces 28 of latches 22 and 24 will engage the locking surface 54 of ring 50. The spring force stored in ring 20 by the expansive force exerted on latches 22 and 24 will force the locking surfaces 28 to ride along the locking surface 54 and force the member 14 into its final position and lock it in such position. Member 14 is formed with an intermediate tubular portion 66 having an outer diameter somewhat larger than that of tubular extension 56. The tubular portions 56 and 66 are joined to each other by an inclined ring portion 68 of which the outer surface will be forced into sealing engagement with the square edge of the inner end 70 of the thickened wall portion 60. In the locked position, the end face 64 of member 56 is spaced slightly from the inclined surface 62 so as not to interfere with the sealing engagement of members 68 and 70. As the members 10 and 14 move into the final locked and sealed position under the force exerted by the spring ring 20, an audible "click" is produced giving a definite indication that the locking and sealing has been completed and that the members of the coupling are fully mated. Such locking and sealing is so secure that accidental separation of the coupled members is virtually impossible.

Figure 4:
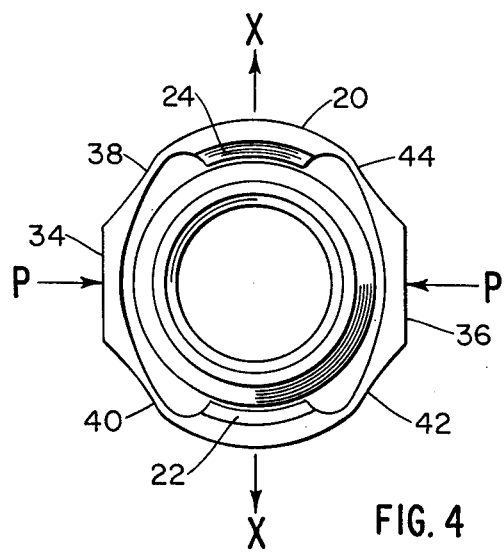
FIG. 4 is a view similar to that of FIG. 3 showing the end ring of the female member with pressure applied to release its latches from the locking ring of the male member.

When it is desired to separate the coupled members, a firm compressive force is exerted on the finger pads 34 and 36, which produces the action described above for FIG. 4, to release the latches 22 and 24 from the locking ring 50 whereupon the male coupling member 14 may be readily separated from the female coupling member 10. It will be noted that the maximum outer diameter of ring 50 is substantially less than the inner diameter of the ring 20 in its state for maximum compression, as shown in FIG. 4, so as to permit such action to occur without the inner wall of ring 20 coming in contact with ring 50.

Figure 5:
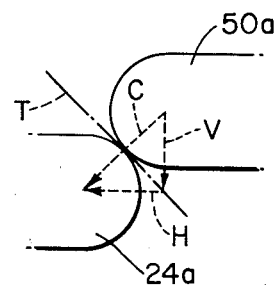
FIG. 5 is a diagrammatic view of a modified shape for the latching and locking members.

It is to be understood that the structure described above represents a preferred embodiment of the invention and that various modifications may be made within the scope of the appended claims. For example, although the preferred embodiment comprises flat lead surfaces 26 for the latches 22 and 24 and a lead surface 52 on the ring 50, all such surfaces being inclined at substantially the same angle with respect to the axial direction through the ring 20, such surfaces may have other configurations. For example, either the lead surfaces on the latches or the lead surface on the locking ring, or both, may be curved or may have angles of inclination which are not all equal. The same is true for the locking surfaces 28 and 54. The significance of the above may be better understood by referring to FIG. 5, which is a diagrammatic showing of a modified cross-section 50a of a locking ring and a modified cross-section 24a of a latch. Each of these cross-sections presents a circular profile for the ring and for the latch. The tangent T to the contacting surfaces at their points of contact is at an angle which is inclined to the axial application of the coupling force V through the device. Thus a force C at right angles to the tangent is exerted between 50a and 24a. This resolves into the vertical force V and a horizontal force H which comprises the desired expansive force to spread the latches as previously explained for FIG. 4. From this it will be seen that as long as the profiles of latches 22 and 24 and ring 50 contact each other along a surface, either on the ring or on the latches, which surface, or the tangent to which is inclined at an angle with respect to the axial direction through the ring 20, the desired forces either for spreading the latches or for forcing the member 14 into its locked position result. For the purpose of this invention any such surface can be termed as being "inclined" with respect to said axial direction, and the term "inclined" will be used in this sense in the appended claims.

Figure 3:
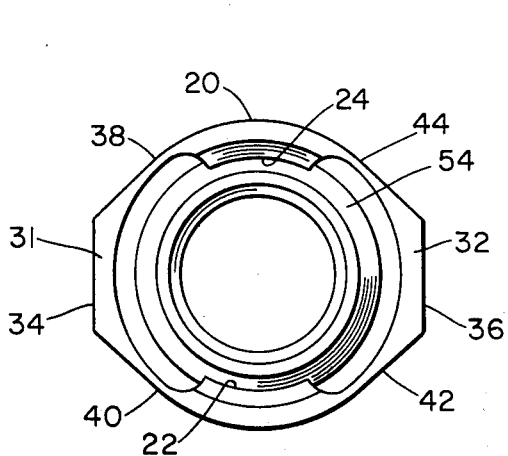
FIG. 3 is an end view of the arrangement of FIG. 2 taken in the direction of the arrows 3—3.
Figure 6:
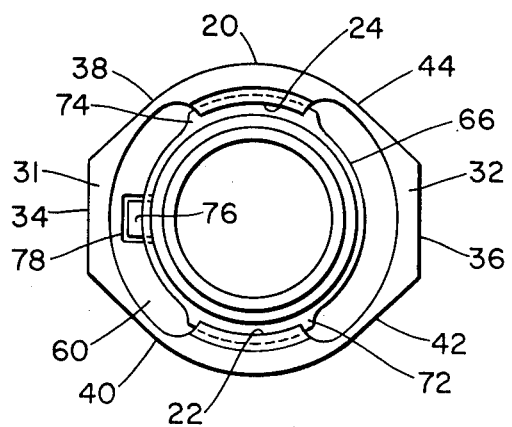
FIG. 6 is a view similar to that of FIG. 3, showing a modification in which the male locking ring is replaced by a pair of opposed locking projections and the coupling members are keyed against rotation.

In addition, instead of producing fluid-tight seals between square edge of face 70 and inclined surface 68, the abutting surfaces may each be flat. Also sealing members, such as O-rings might be located between such surfaces, or between the tubular member 56 and bore 58. Instead of the locking member of the male coupling member 14 being in the form of a ring 50, as in FIG. 3, its locking function may be accomplished by the use of two separate opposing projections 72 and 74 as shown in FIG. 6. In this modification the projections 72 and 74 would substantially agree with the contour of the latches 22 and 24 of the female coupling member 10. This form could be used where the coupling members are keyed to each other, a by a key 76 on the tubular extension 56 entering a keyway 78 formed in the inner wall of thickened wall member 60. Such keyed arrangement might be used where it is desired to prevent relative rotation and to maintain registration between members 10 and 14.

Figure 7:
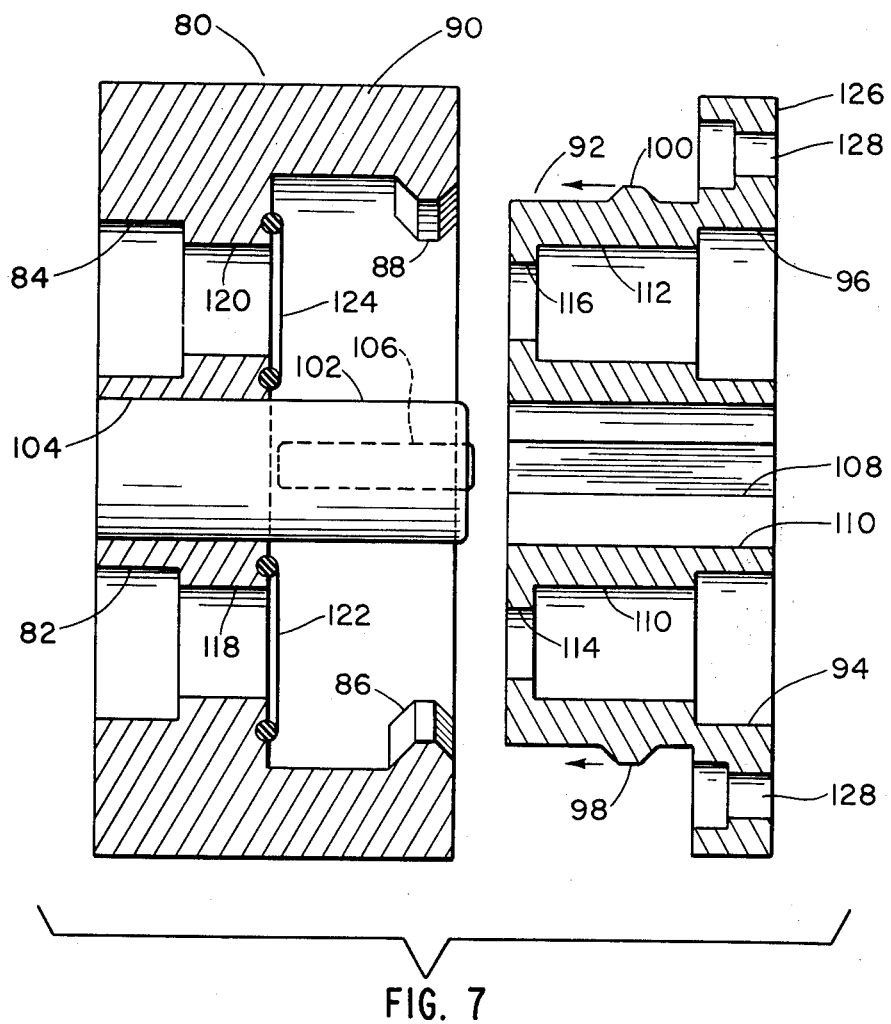
FIG. 7 is a view similar to that of FIG. 1, showing a multiple conduit coupling modification.

The principles of this invention readily lend themselves to various types of multiple conduit couplings as shown, for example, in FIG. 7. In this modification, the female coupling member 80 is provided with a plurality of bores 82, 84 etc, each of which is adapted to receive a conduit in a manner similar to that described with respect to members 10 and 12 in FIG. 3. Typically, six such bores are arranged 60° apart from each other around the axis of member 80 although any other convenient number may be used. Latches 86 and 88, corresponding to latches 22 and 24 of the previously described embodiment, are disposed on the interior of ring 90, corresponding to ring 20. As in the case of ring 20, ring 90 is formed as a continuous ring with thickened and thinned wall portions to accomplish substantially the same functions as ring 20. Similarly, in FIG. 7, the male coupling member 92 is provided with a plurality of bores 94, 96, etc., corresponding in number and portion with bores 82, 84 etc., so that the conduits secured in bores 82, 84, etc., may be coupled with conduits secured in bores 94, 96, etc. As in the modification of FIG. 6, the male locking function is preferrably performed by a pair of locking projections 98 and 100 wich are adapted to cooperate with the female latches 86 and 88. In order to ensure the proper alignment of bores 82, 84, 94, 96, etc., female member 80 is provided with a rod 102 secured in a bore 104 formed with the base of member 80. One side of rod 102 carries a key 106 which is adapted to enter a keyway 108 formed in the inner wall of a bore 110 which is aligned with bore 104 in the coupled position. The bores 94 and 96 lead into passages 110 and 112 which terminate in openings 114 and 116. Likewise bores 82 and 84 lead into passages 118 and 120 which are adapted to be aligned with openings 114 and 116 respectively. O rings 122 and 124 set into the surfaces of member 80 surrounding passages 118 and 120 cooperate with the surfaces of member 92 surrounding openings 114 and 116 to ensure fluid tight dealing between the aligned openings and passages. Male member 92 may be provided with a flange 126 supplied with bolt holes 128 so that male member 92 may be bolted to a bulkbead or any other convenient mounting member.

Other sealing arrangements will also suggest themselves. In addition to providing a sealed coupling between fluid conduits, the invention may be used for any type of quick detachable coupler, such as for electrical couplers, where it may be desired to obtain the advantages provided by this invention. The finger pads 36 may be provided with non-slip surfaces or otherwise configured to assist in gripping the coupler. The coupling members and the devices which they connect are not necessarily cylindrical in cross-section and therefore the terms "tube" and "tubular" are used herein in a general sense which includes pipes and conduits of non-circular cross-section. Various other modifications will suggest themselves to those skilled in the art.

What is claimed is:

1. A quick detachable coupler comprising:
  a. a female coupling member having one end thereof in the form of a stiff, continuous ring of resilient material provided with a pair of opposed latches projecting inwardly of said ring, said ring also being provided with a pair of external pressure receiving portions disposed opposite each other across said ring in a direction transverse to the direction along which said latches are disposed, and
  b. a male coupling member having an extenal locking projection extending outward of said male coupling member a distance which is greater than the spacing between said latches in the normal condition of said ring, whereby in the coupled position said locking projection is locked behind said latches;
  c. the portions of said ring intermediate said latches and said pressure receiving portions having a flexibility to permit said ring to be sprung inwardly, along said transverse direction upon the application of pressure to said pressure receiving portions, sufficiently to move said latches outwardly to a position greater than the distance across said locking projection, whereby said male member may be separated from said female member;
  d. said latches having lead surfaces and locking surfaces, said locking surface located opposite the lead surfaces and said projection having a lead surface and a locking surface said locking surface on said projection located on the side of said projection opposite its lead surface, at least one of said locking surfaces being inclined with respect to the axial direction through said ring, said male and female coupling members, latches and projections being so constricted and arranged that when said locking surfaces of said latches are in engagement with said locking surface of said projection, said male and female coupling members are constantly urged toward each other.

2. A coupler as in claim 1 in which the wall of said ring is thinner intermediate said latches and pressure receiving portions than at said latches and pressure receiving portions.

3. A coupler as in claim 1 in which, the lead surface of said projection is adapted to engage the lead surfaces of said latches upon said male member being inserted into said female member, one of said lead surfaces being inclined with respect to the axial direction through said ring.

4. A coupler as in claim 3 in which both said locking surfaces are inclined with respect to the axial direction through said ring.

5. A coupler as in claim 3 in which each of said lead surfaces is a flat surface, each of said flat surfaces being inclined at substantially the same angle with respect to the axial direction through said ring.

6. A coupler as in claim 4 in which each of said locking surfaces is a flat surface, each of said flat surfaces being inclined at substantially the same angle with respect to the axial direction through said ring.

7. A coupler as in claim 1 in which the body of said female member has a thicker wall than the wall of said ring, said female member being provided with stress-relief slots intermediate said walls.

8. A coupler as in claim 3 in which said male member is provided at its lead end with a tubular extension, said female member being pivoted interiorly thereof with a bore into which said tubular extension is adapted to fit snugly, the distance between the lead end of said tubular extension and the locking projection on said male member being greater than the distance between the entrance to said bore and the lead surfaces of said latches, whereby said lead end of said tubular extension enters said bore before the lead surface on said projection comes into contact with the lead surfaces on said latches.

9. A coupler as in claim 8 in which said tubular extension has means thereon to make sealing contact against said entrance to said bore in its fully inserted position.

10. A coupler as in claim 1 in which said external locking projection is in the form of a continuous ring surrounding said male coupling member.

11. A coupler as in claim 1 in which said external locking projection is in the form of a pair of opposed latches projecting outwardly of said male coupling member.

12. A coupler as in claim 11 in which said male and female coupling members are provided with cooperating keyway means adapted to orient said coupling members so that the latches on said female member and the latches on said male member are in alignment with each other in the coupled position.

13. A coupler as in claim 1 in which said female and male members are each provided with a plurality of openings each opening being adapted to have an external conduit connected thereto.

* * * * *

UNITED STATES PATENT OFFICE
CERTIFICATE OF CORRECTION

Patent No. 3,990,727                 Dated November 9, 1976

Inventor(s) Stephen Francis Gallagher

It is certified that error appears in the above-identified patent and that said Letters Patent are hereby corrected as shown below:

COLUMN 5, Line 57, after "locking" delete "surface" and substitute --surfaces--

COLUMN 6, Line 34, after "being" delete "pivoted" and substitute --provided--

COLUMN 6, Line 45, after "thereon" insert --adapted--

Signed and Sealed this

Seventh Day of June 1977

[SEAL]

Attest:

RUTH C. MASON  
Attesting Officer

C. MARSHALL DANN  
Commissioner of Patents and Trademarks